United States Patent [19]

Bondinell et al.

[11] Patent Number: 4,824,839

[45] Date of Patent: Apr. 25, 1989

[54] SULFINYL AND SULFONYL SUBSTITUTED 2,3,4,5 TETRAHYDRO-1H-3-BENZAZEPINES AND THEIR USE IN TREATING GASTROINTESTINAL MOTILITY DISORDERS

[75] Inventors: William E. Bondinell; Herbert S. Ormsbee, III, both of Wayne, Pa.

[73] Assignee: SmithKline Beckman Corporation, Philadelphia, Pa.

[21] Appl. No.: 167,663

[22] Filed: Mar. 14, 1988

Related U.S. Application Data

[63] Continuation-in-part of Ser. No. 13,103, Feb. 10, 1987, abandoned, which is a continuation-in-part of Ser. No. 811,789, Dec. 20, 1985, Pat. No. 4,659,706, and Ser. No. 36,403, Apr. 9, 1987, which is a continuation-in-part of Ser. No. 13,103.

[51] Int. Cl.[4] .................... C07D 223/16; A61K 31/55
[52] U.S. Cl. .................................... 514/213; 540/595
[58] Field of Search ......................... 540/595; 514/213

[56] References Cited

U.S. PATENT DOCUMENTS 3,689,649  9/1972  Dietrich .............................. 514/213
4,514,394  4/1985  Chambers et al. .................. 540/595

*Primary Examiner*—David B. Springer
*Attorney, Agent, or Firm*—Linda E. Hall; Janice E. Williams; Alan D. Lourie

[57] ABSTRACT

Sulfinyl and sulfonyl substituted 3-benzazepine compounds are useful in treating gastrointestinal motility disorders and emesis. A particular compound of this invention is 7-methylsulfonyl-2,3,4,5-tetrahydro-1H-3-benzazepine.

19 Claims, No Drawings

SULFINYL AND SULFONYL SUBSTITUTED 2,3,4,5 TETRAHYDRO-1H-3-BENZAZEPINES AND THEIR USE IN TREATING GASTROINTESTINAL MOTILITY DISORDERS

This application is a continuation-in-part of U.S. patent application Ser. No. 013,103 filed Feb. 10, 1987, abandoned, which in turn is a continuation-in-part of Ser. No. 811,789 filed Dec. 20, 1985, U.S. Pat. No. 4,659,706 and also a continuation-in-part of U.S. patent application Ser. No. 036,403 filed Apr. 9, 1987, which is a continuation-in-part of U.S. patent application Ser. No. 013,103.

This invention relates to new sulfinyl and sulfonyl substituted benzazepine compounds, pharmaceutical compositions containing them and methods of treating gastrointestinal motility disorders and emesis by administering these compounds.

The compounds of this invention have utility in the treatment of gastrointestinal diseases, in particular gastrointestinal motility disorders and emesis. The compounds are useful therapeutically for gastroesophageal reflux disease and disorders of delayed gastric emptying of various etiologies including diabetes, surgery, and idiopathic delayed emptying. The compounds may also be useful in treating disorders of upper GI motility, aspiration, early satiety, anorexia nervosa, and in diagnostic radiology or to facilitate intubation.

The compounds of this invention are represented by the following formula (I):

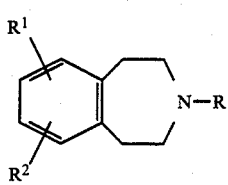

in which:

R is hydrogen, $C_1$–$C_6$alkyl or $C_3$–$C_5$alkenyl;
$R^1$ is $SOR^3$, $SO_2R^3$ or $SO_1NB_4R^5$;
$R^2$ is hydrogen, halogen, $CF_3$, $C_1$–$C_6$alkyl or $R^6O$—;
$R^3$ is $C_1$–$C_6$alkyl or $CF_3$;
$R^4$ and $R^5$ are hydrogen or $C_1$–$C_6$alkyl; and
$R^6$ is hydrogen, $C_1$–$C_6$alkyl or $C_1$–$C_6$alkanoyl,
provided that when $R^1$ is $SO_2NH_25$ $R^2$ is $R^6O$—, halogen, $CF_3$ or $C_1$–$C_6$alkyl, or a pharmaceutically acceptable acid addition salt thereof.

Particular compounds of formula (I) are those in which $R^1$ is in the 7-position. Further particular compounds of formula (I) are those in which $R^1$ is in the 7-position and $R^2$ is in the 8-position.

A group of compounds of formula (I) is that in which $R^1$ is $SO_2R^3$ or $SO_2NR^4R^5$, $R^2$ is hydrogen, alkoxy or hydroxy, $R^3$ is methyl and R is hydrogen and, in addition, $R^1$ may be in the 7-position and $R^2$ may be in the 8-position.

Specific compounds of this invention are:
8-hydroxy-7-methylsulfonyl-2,3,4,5-tetrahydro-1H-3-benzazepine;
7-methylsulfonyl-2,3,4,5-tetrahydro-1H-3-benzazepine;
8-hydroxy-7-(N-methylsulfamoyl)-2,3,4,5-tetrahydro-1H-3-benzazepine;
8-methoxy-7-methylsulfonyl-2,3,4,5-tetrahydro-1H-3-benzazepine;
6-sulfamoyl-2,3,4,5-tetrahydro-1H-3-benzazepine;
7-sulfamoyl-2,3,4,5-tetrahydro-1H-3-benzazepine.

The process for preparing a compound of the formula (1) or a pharmaceutically acceptable acid-addition salt thereof, comprises:

(a) for compounds where $R^1$ is $SOR^3$ and $SO_2R^3$, reacting a compound of the formula (II):

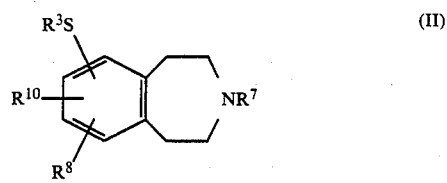

wherein $R^3$ is as hereinbefore defined, $R^7$ is a N-protecting group, $R^8$ is hydrogen, $C_1$–$C_6$alkyl, halogen with $CF_3$ or $OR^9$ where $R^9$ is an O-protecting group and $R^{10}$ is hydrogen or bromo, with an oxidizing agent;

(b) for compounds where $R^1$ is $SO_2R^3$ where $R^3$ is $C_1$–$C_6$alkyl, reducing a compound of the formula (III):

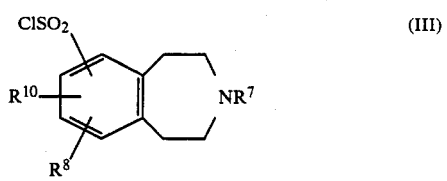

wherein $R^7$ and $R^8$ are as hereinbefore defined and $B^{10}$ is hydrogen or bromo, with sodium sulfite and reacting with a $C_1$–$C_6$ alkylating agent; or (c) for compounds where $R^1$ is $SO_2NR^4R^5$, reacting a compound of the formula (III) as hereinbefore defined with an amine: $R^4R^5NH$ where $R^4$ and $R^5$ are as hereinbefore defined; and thereafter if necessary:
  (i) debrominating the benzazepine ring when $R^{10}$ is bromo,
  (ii) removing a N-protecting group,
  (iii) alkylating or alkenylating the secondary amino group of the benzazepine ring,
  (iv) removing a O-protecting group,
  (v) alkylating or alkanoylating the hydroxy group of the benzazepine ring,
  (vi) forming a pharmaceutically acceptable acid addition salt.

A compound of the formula (II) is suitably treated with an oxidizing agent such as hydrogen peroxide or a peracid such as 3-chloroperbenzoic acid, in a solvent such as acetic acid. One equivalent of the oxidizing agent gives the sulfinyl compounds and two equivalents gives the sulfonyl compounds.

Suitably a compound of the formula (III) is treated with sodium sulfite in aqueous sodium bicarbonate and then with a $C_1$–$C_6$ alkylating agent. Suitable alkylating agents include $C_1$–$C_6$alkyl halides, for example $C_1$–$C_6$ alkyl bromides and iodides.

A compound of the formula (III) is suitably reacted with an amine ($R^6R^7NH$) in a solvent such as dichloromethane. When $R^6$ and $R^7$ are hydrogen, preferably ammonium hydroxide is used.

In the compounds of the formulae (II) and (III) the following combinations of substituents are preferable.

$R^{10}$ is hydrogen when the groups $R^8$ and $ClSO_2$ or $R^3S$ are meta or para to each other.

$R^{10}$ is 9-bromo when $R^8$ is in the 6-position and $ClSO_2$ or $R^3S$ is in the 7-position.

$R^{10}$ is 8-bromo when $R^8$ is in the 7-position and $ClSO_2$ or $R^3S$ is in the 6-position.

$R^{10}$ is hydrogen when $R^8$ is in the 8-position and $ClSO_2$ or $R^3S$ is in the 7-position.

The subsequent steps of debromination, N-deprotection, N-alkylation, N-alkenylation, O-deprotection, O-alkylation and O-alkanoylation may be carried out by standard methods and may be carried out in various order of steps to prepare the desired compounds.

Compounds of the formula (II) can be prepared by the following general routes:

(a) for compounds where $R^3$ is $C_1$-$C_6$alkyl, by treating a compound of the formula (IV)

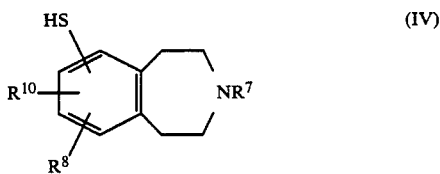

where $R^7$, $R^8$ and $R^{10}$ are as hereinbefore defined, with a $C_1$-$C_6$ alkylating agent for example a $C_1$-$C_6$alkyl halide or a $C_1$-$C_6$dialkyl sulfate;

(b) by treating a compound of the formula (V):

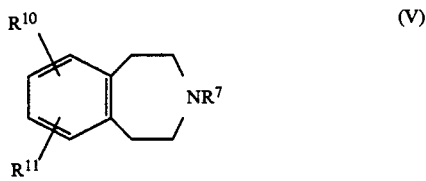

wherein $R^{10}$ is bromo, $R^{11}$ is $R^8$ and $R^7$ and $R^8$ are as hereinbefore defined, with butyllithium and with either $(R^3S)^2$ or $R^3SCl$;

(c) for compounds where $R^8$ is $OR^9$, by treating a compound of the formula (V) wherein $R^{11}$ is OH, $R^{10}$ is hydrogen or bromo and $R^7$ is as hereinbefore defined, with $R^3SCl$ and then protecting the free hydroxyl group;

(d) for compounds where $R^3$ is trifluoromethyl, by treating a compound of the formula (II) wherein $R^3$ is methyl, with chlorine in the presence of cumene and then with antimony trifluoride and antimony pentachloride.

A compound of the formula (IV) can be prepared by reducing a compound of the formula (III). Suitably the reduction is performed with stannous chloride.

Compounds of the formula (III) can be prepared as follows:

(a) by treating a compound of the formula (V) where $R^{10}$ is hydrogen or bromo, $R^{11}$ is $R^8$ and $R^7$ and $R^8$ are as hereinbefore defined with chlorosulfonic acid; and (b) by treating a compound of the formula (II) as hereinbefore defined with chlorine and aqueous acetic acid.

Suitable N-protecting groups for compounds of the formulae (II), (III), (IV) and (V) include acyl groups such as acetyl, trifluoroacetyl, benzoyl, methoxycarbonyl or benzyloxycarbonyl. Suitable O-protecting groups for compounds of the formulae (II), (III), (IV) and (V) include $C_1$-$C_6$alkyl and benzyl. These groups can be introduced in standard manner.

The compounds of the formula (V) can be prepared using methods known in the art, for example by bromination of a compound of the formula (V) wherein $R^{10}$ is hydrogen, or by the methods illustrated in Examples 1, 9 and 10 hereinafter described.

The compounds of formula (I) form pharmaceutically acceptable acid addition salts with organic or inorganic acids. Examples of these acids are hydrochloric, hydrobromic, sulfuric, phosphoric, acetic, tartaric, citric, maleic, lactic, oxalic, succinic, methanesulfonic, and benzenesulfonic acids. The salts are formed according to methods known to the art. If the product is isolated as an acid addition salt, it may be treated with an inorganic or organic base, such as aqueous sodium hydroxide, sodium carbonate, triethylamine, etc., and converted to the corresponding free base. The base can then be treated with an appropriate acid, for example in an aqueous miscible solvent, such as a lower alkanol preferably methanol or ethanol, to give the desired salt.

The effect of the pharmacologically active compounds of this invention on gastrointestinal motility is demonstrated in test procedures as follows:

(1) an increase in resting pressure of the lower esophageal sphincter (LES) in dogs; and (2) an increase in the rate of gastric emptying in rats.

Method for Determination of LES Pressure in the Anesthetized Dog

Mongrel or beagle dogs, male and female, are anesthetized using sodium pentobarbital (35.0 mg/kg., i.v.). Sodium pentobarbital is then continuously infused (approximately 6.0 mg/kg/hr) to maintain deep anesthesia. Blood pressure is monitored via a catheter surgically implanted into the femoral artery and attached to a GouldStatham P23ID transducer. A catheter is also implanted into the femoral vein to administer test drugs. Respiration is maintained by an endotracheal tube attached to a respirator. A continuously perfused manometric catheter system including a Dent sleeve to measure sphincter pressure (Dent, *Gastroenterology* 71: 263-267, 1976) is inserted into the esophagus and positioned so that intraluminal pressure is recorded from the body of the esophagus, the lower esophageal sphincter (LES) and the fundus of the stomach. The Dent sleeve catheter is perfused at a rate of 0.5 ml of water per minute for each lumen of the catheter by using an Arndorfer Hydraulic Capillary Infusion System. A cannula is implanted into the gastric antrum to allow drainage of the perfusate solution and prevent intestinal distension. Continuous tracings of esophageal, LES and fundus pressure are monitored on a Grass Polygraph (Model 7D). Correct positioning of the Dent sleeve is verified by noting a high pressure zone at the LES and by administration of an intravenous dose of 5-hydroxytryptamine (usually 10-15 mcg/kg) which contracts the LES while having little or no recordable effect on either the body of the esophagus or the fundus. After verification of placement of the sleeve, the animal is allowed to stabilize for approximately 30 minutes.

Compounds are administered intravenously, intraduodenally or intragastrically. In most cases, succeeding doses of the same or different compounds are given only after the LES pressure has returned to approximate pre-dosing baseline values. In all cases, the magnitude of change in LES pressure is determined from the baseline pressure immediately prior to each treatment to the maximum pressure during treatment. Since the compounds used usually produce an immediate effect on LES pressure, no pretreatment time prior to measurement is necessary during this testing.

Direct assay techniques are used to estimate an Effective Dose 20 ($ED_{20}$) for the test compound in individual animals. The mean $ED_{20}$ and 95 PERCENT confidence limits are determined using the individual $ED_{20}$ values from a group of animals (N=3) that received the same treatment. The $ED_{20}$ is the dose which increases LES pressure 20 mm Hg. The $ED_{20}$'s of the 8-hydroxy-7-sulfamoyl, 8-hydroxy-7-(N-methylsulfamoyl) and 8-hydroxy-7-methylsulfonyl compounds of Examples 1, 2 and 4 are 50.7, 4.0 and 27.0 mcg/kg, i.v., respectively. The $ED_{20}$'s of the 7-methylsulfonyl-8-methoxy and 7-methylsulfonyl compounds are 33.9 and 40.3 mcg/kg, i.d. respectively.

Gastric Emptying in the Rat

Fasted rats are administered 0.5 Ci of $Na_2{}^{51}CrO$ (0.2 ml vol) into the stomach with an oral feeding tube. Compounds for evaluation or vehicle controls are administered either 15 minutes before (oral administration) or simultaneously with (intravenous administration) the test meal. After 35 minutes the rats are killed by cervical dislocation and the stomach is removed. Gastric emptying is measured from the amount of $^{51}Cr$ remaining in the stomach at death. In this test, the compound of Example 4 at a dose of 0.5 mg/kg, i.v. doubled the rate of gastric emptying as compared to control.

Method for Determination of the Anti-emetic Effect in the Conscious Dog

Compounds are administered orally or parenterally to proven apomorphine-sensitive dogs of either sex. After the appropriate time has elapsed (determined by a peak time study), apomorphine hydrochloride (0.1 mg/kg, s.c.) is administered and the frequency of emesis is observed and recorded for the next forty minutes. Emesis is defined as the actual expulsion of stomach contents.

The control group of dogs, also apomorphine-sensitive, receive the test vehicle and apomorphine hydrochloride (0.1 mg/kg, s.c.) Emesis is recorded as with the test animals.

The mean frequency of emesis for the control and test groups is calculated. A value for each test group is then obtained which expresses the percentage increase or decrease in frequency of emesis relative to controls. An effective dose-50% is calculated. The $ED_{50}$ refers to the dose that decreases emesis induced by apomorphine by 50%.

This invention also includes pharmaceutical compositions for treatment of gastrointestinal motility disorders comprising a compound of formula (I), 6-sulfamoyl-2,3,4,5-tetrahydro-1H-3-benzazepine, or 7-sulfamoyl-2,3,4,5-tetrahydro-1H-3-benzazepine, or a pharmaceutically acceptable acid addition salt thereof and a pharmaceutically acceptable carrier.

The pharmacologically active compounds of formula (I) can be administered orally or parenterally. Preferably, these compounds are administered in conventional dosage unit forms prepared by combining an appropriate dose of the compound with standard pharmaceutical carriers. The dosage units will contain the active ingredient in an effective amount selected from about 1 mg. to about 250 mg., preferably 10 mg. to 100 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a trouche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul or an aqueous or nonaqueous liquid suspension.

The pharmaceutical compositions are prepared by conventional techniques involving procedures such as mixing, granulating and compressing when necessary or variously mixing and dissolving the ingredients as appropriate to the desired composition.

The method of treating gastrointestinal motility disorders in accordance with this invention comprises administering internally to a subject in need of said particular treatment an effective amount of a compound of formula (I), in particular, 7-methylsulfonyl-2,3,4,5-tetrahydro-1H-3-benzazepine, 6-sulfamoyl-2,3,4,5-tetrahydro- 1H-3-benzazepine, 7-sulfamoyl-2,3,4,5-tetrahydro-1H-3-henzazepine, or 8-methoxy-7-methylsulfonyl-2,3,4,5-tetrahydro-1H-3-benzazepine or a pharmaceutically acceptable acid addition salt thereof.

The method of treating and preventing emesis in accordance with this invention comprises administering internally to a subject in need of said treatment an effective amount of a compound of formula (I), in particular 8-hydroxy-7-methylsulfonyl-2,3,4,5-tetrahydro-1H-3-benzazepine.

The compound will preferably be administered in a dosage unit form orally or parenterally. Advantageously equal doses will be administered one to four times daily with the daily dosage regimen being from about 1 mg. to about 1000 mg., preferably from 10 mg. to 400 mg. The method described above is useful for treating gastrointestinal motility disorders.

One skilled in the art will recognize that in determininq the amounts of the compound needed to produce the desired pharmacological effect without toxic side effects, the activity of the particular compound as well as the size of the host animal must be considered.

The following examples illustrate the invention but are not to be construed as limiting the scope thereof. Temperatures are in degrees Centigrade unless otherwise stated.

EXAMPLE 1

8-Hydroxy-7-sulfamoyl-2,3,4,5-tetrahydro-1H-3-benzazepine.

A mixture of 3-methoxyphenylacetic acid (47.7 g, 0.287 m), thionyl chloride (50 ml) and N,N-dimethylformamide (6 drops) in toluene (500 ml) was stirred for 16 hours at 25° and concentrated in vacuo to afford 3-methoxyphenylacetyl chloride. The acetyl chloride was dissolved in chloroform (100 ml) and added to a solution of aminoacetaldehyde dimethyl acetal (32.1 g, 0.306 m) and triethylamine (32.4 g, 0.320 m) in chloroform (500 ml) stirred at 5°. The mixture was stirred at 25° for 16 hours, washed with water, 1.5 N hydrochloric acid and water, dried with magnesium sulfate and concentrated in vacuo to give N-(2,2-dimethoxyethyl)-3-methoxybenzeneacetamide.

A solution of the benzeneacetamide (70 g, 0.277 m) in acetic acid (180 ml) was added with stirring to concentrated hydrochloric acid (120 ml). The mixture was stirred for 16 hours, diluted with ice/water and filtered. The filter cake was dissolved in methylene chloride which was washed with water, dried with magnesium sulfate and concentrated in vacuo to give 2,3-dihydro-8-methoxy-2-oxo-1H-3-benzazepine.

A mixture of 2,3-dihydro-8-methoxy-2-oxo-1H-3-benzazepine (12 g, 0.063 m) and 10% palladium-on-carbon (1.2 g) in acetic acid (200 ml) was shaken in an atmosphere of hydrogen (60 psi), degassed, filtered and concentrated in vacuo. The residue was dissolved in methylene chloride, washed with water, dried with magnesium sulfate and concentrated in vacuo. The residue was triturated with ether and filtered to give 8-methoxy-2-oxo-2,3,4,5-tetrahydro-1H-3-benzazepine.

A suspension of 8-methoxy-2-oxo-2,3,4,5-tetrahydro-1H-3-benzazepine (20.4 g, 0.105 m) in tetrahydrofuran (500 ml) was added to 1 M borane in tetrahydrofuran (300 ml) stirred at 5°. The mixture was heated to reflux for 2 hours, cooled, treated with 3N hydrochloric acid (300 ml), concentrated in vacuo to remove tetrahydrofuran and heated to reflux for 1 hour. The mixture was concentrated in vacuo, filtered and the filter cake was dissolved in methanol, heated to reflux, dried with magnesium sulfate and concentrated in vacuo to afford 7-methoxy-2,3,4,5-tetrahydro-1H-3-benzazepine hydrochloride, m.p. 229°–231°.

A mixture of 7-methoxy-2,3,4,5-tetrahydro-1H-3-benzazepine hydrochloride (4.3 g, 0.02 m) and sodium acetate (3.3 g, 0.04 m) in acetic anhydride (13 ml) was refluxed and stirred for 16 hours, concentrated in vacuo and partitioned between methylene chloride and water. The organic phase was dried with magnesium sulfate, filtered and concentrated in vacuo to give 3-acetyl-7-methoxy-2,3,4,5-tetrahydro-1H-3-benzazepine, m.p. 89°–90°.

3-Acetyl-7-methoxy-2,3,4,5-tetrahydro-1H-3-benzazepine (2.3 g, 0.01 m) was added to chlorosulfonic acid (6 ml) which was stirred at 0°; the mixture was allowed to warm to 25° and stirred for 16 hours. The reaction was carefully poured into ice water and extracted with methylene chloride. The methylene chloride extracts were combined, washed, dried with magnesium sulfate and concentrated in vacuo to give 3-acetyl-7-chlorosulfonyl-8-methoxy-2,3,4,5-tetrahydro-1H-3-benzazepine, m.p. 153°–160°.

3-Acetyl-7-chlorosulfonyl-8-methoxy-2,3,4,5-tetrahydro-1H-3-benzazepine (3 g, 0.007 m) was treated with concentrated ammonium hydroxide (10 ml), stirred for 2 hours and filtered to give 3-acetyl-8-methoxy-7-sulfamoyl-2,3,4,5-tetrahydro-1H-3-benzazepine, m.p. 260°–263°.

The sulfonamide (2.3 g, 0.007 m) was suspended in 3N hydrochloric acid and heated to reflux for 16 hours. The mixture was concentrated in vacuo and the residue crystallized from methanol to give 8-methoxy-7-sulfamoyl-2,3,4,5-tetrahydro-1H-3-benzazepine hydrochloride, m.p. 270°–274°.

8-Methoxy-7-sulfamoyl-2,3,4,5-tetrahydro-1H-3-benzazepine hydrochloride (1.5 g, 0.005 m) was dissolved in 48% hydrobromic acid (15 ml), refluxed for 2 hours and concentrated in vacuo. The residue was triturated with acetone and then recrystallized from methanol to give 8-hydroxy-7-sulfamoyl-2,3,4,5-tetrahydro-1H-3-benzazepine hydrobromide, m.p. 315°–320° (decomp.).

EXAMPLE 2

8-Hydroxy-7-(N-methylsulfamoyl)-2,3,4,5-tetrahydro-1H-3-benzazepine

3-Acetyl-7-chlorosulfonyl-8-methoxy-2,3,4,5-tetrahydro-1H-3-benzazepine (2 g) was stirred with 10 ml of 40% aqueous methylamine, then was treated with hydrochloric acid and concentrated in vacuo to give 8-methoxy-7-(N-methylsulfamoyl)-2,3,4,5-tetrahydro-1H-3-benzazepine hydrochloride. This 8-methoxy-7-(N-methylsulfamoyl) compound was treated with boron tribromide in methylene chloride and then with methanol to give 8-hydroxy-7-(N-methylsulfamoyl)-2,3,4,5-tetrahydro-1H-3-benzazepine hydrobromide, m.p. 130°–135° C.

EXAMPLE 3

8-Hydroxy-7-(N,N-dimethylsulfamoyl)-2,3,4,5-tetrahydro-1H-3-benzazepine

By the procedure of Example 2, using dimethylamine in place of methylamine, 8-methoxy-7-(N,N-dimethylsulfamoyl)-2,3,4,5-tetrahydro-1H-3-benzazepine hydrochloride was obtained which, on treatment with boron tribromide, gave 8-hydroxy-7-(N,N-dimethylsulfamoyl)-2,3,4,5-tetrahydro-1H-3-benzazepine hydrobromide, m.p. 195°–197° C.

EXAMPLE 4

8-Hydroxy-7-methylsulfonyl-2,3,4,5-tetrahydro-1H-3-benzazepine

Method A

3-Acetyl-7-chlorosulfonyl-8-methoxy-2,3,4,5-tetrahydro-1H-3-benzazepine (18 g, 0.056 m) was added in portions to a mixture of sodium sulfite (8.8 g, 0.069 m) and sodium bicarbonate (10.8 g, 0.115 m) in water (36 ml) stirred at 70° C. There was a vigorous evolution of gas after each addition. The mixture was stirred for fifteen minutes, treated with iodomethane (8.5 ml, 0.136 m) and refluxed for forty-five minutes. The mixture was partitioned between methylene chloride and water. The methylene chloride phase was washed with water, dried with sodium sulfate and concentrated in vacuo to give 3-acetyl-8-methoxy-7-methylsulfonyl-2,3,4,5-tetrahydro-1H-3-benzazepine, m.p. 159°–162° C.

Method B

3-Acetyl-7-chlorosulfonyl-8-methoxy-2,3,4,5-tetrahydro-1H-3-benzazepine (4 g, 0.013 m) was dissolved in glacial acetic acid (80 ml), treated with stannous chloride dihydrate (11.6 g, 0.05 m) and concentrated hydrochloric acid (16 ml) and stirred at 75° for 1 hour. The mixture was cooled, poured into ice water and extracted with ethyl acetate. The combined ethyl acetate extract was washed, dried with magnesium sulfate and concentrated in vacuo to give a mixture of 3-acetyl-7-mercapto-8-methoxy-2,3,4,5-tetrahydro-1H-3-benzazepine and the corresponding disulfide.

The crude mixture (3 g) was dissolved in ethanol and treated with sodium borohydride (2 g, 0.05 m) to effect reduction of the disulfide to the mercaptan. Methyl iodide (2 g, 0.014 m) was added and the reaction mixture was stirred at 25° for 1 hour. The mixture was concentrated, partitioned between water and methylene chloride and the combined methylene chloride extract was washed, dried with magnesium sulfate and concentrated in vacuo to give 3-acetyl-8-methoxy-7-methylthio-2,3,4,5-tetrahydro-1H-3-benzazepine, m.p. 138°–140°.

3-Acetyl-8-methoxy-7-methylthio-2,3,4,5-tetrahydro-1H-3-benzazepine (1.1 g, 0.004 m) dissolved in chloride (10 ml) was treated with 3-chloromethylene perbenzoic acid (1.4 g, 0.008 m) and stirred for 1 hour. The mixture was extracted with 5% aqueous sodium carbonate, washed with water, dried with magnesium sulfate and concentrated in vacuo to give 3-acetyl-8-methoxy-7-methylsulfonyl-2,3,4,5-tetrahydro-1H-3-benzazepine, m.p. 162°–164°.

3-Acetyl-8-methoxy-7-methylsulfonyl-2,3,4,5-tetrahydro-1H-3-benzazepine (1 g, 0.003 m), prepared as in Method A or B, in 48% hydrobromic acid (15 ml) was heated to reflux for 16 hours and concentrated in vacuo. The residue was triturated with acetone and recrystallized from methanol-water to give 8-hydroxy-7-methylsulfonyl-2.3.4.5 -tetrahydro-1H-3-benzazepine hydrobromide, m.p. 300° (decomp.).

Alternatively, 3-acetyl-8-methoxy-7-methylsulfonyl-2,3,4,5-tetrahydro-1H-3-benzazepine was treated with 3N hydrochloric acid to give 8-methoxy-7-methylsulfonyl-2,3,4,5-tetrahydro-1H-3-benzazepine hydrochloride, m.p. 228.5°–229.5°. Refluxing this compound with 48% hydrobromic acid gave 8-hydroxy-7-methylsulfonyl-2,3,4,5-tetrahydro-1H-3-benzazepine hydrobromide.

EXAMPLE 5

8-Hydroxy-7-methylsulfinyl-2,3,4,5-tetrahydro-1H-3-benzazepine

Following the general procedure of Example 4 Method B, 3-acetyl-8-methoxy-7-methylthio-2,3,4,5-tetrahydro-1H-3-benzazepine is reacted with one equivalent of 3-chloroperbenzoic acid to give 3-acetyl-8-methoxy-7-methylsulfinyl-2,3,4,5-tetrahydro-1H-3-benzazepine. Following the procedure of Example 4, 3-acetyl-8-methoxy-7-methylsulfinyl-2,3,4,5-tetrahydro-1H-3-benzazepine is reacted with 3N hydrochloric acid to give 8-methoxy-7-methylsulfinyl-2,3,4,5-tetrahydro-1H-3-benzazepine hydrochloride. This methoxy compound is treated with pyridine hydrochloride to give 8-hydroxy-7-methylsulfinyl-2,3,4,5-tetrahydro-1H-3-benzazepine hydrochloride.

EXAMPLE 6

8-Hydroxy-3-methyl-7-methylsulfonyl-2,3,4,5-tetrahydro-1H-3-benzazepine

A mixture of 8-methoxy-7-methylsulfonyl-2,3,4,5-tetrahydro-1H-3-benzazepine hydrochloride (1 g, 3.5 mmol), 37% aqueous formaldehyde (1.1 g) and platinum oxide (0.1 g) in ethanol (25 ml) was shaken under an atmosphere of hydrogen (60 psi). The mixture was degassed, filtered and concentrated at reduced pressure to give 3-methyl-8-methoxy-7-methylsulfonyl-2,3,4,5-tetrahydro-1H-3-benzazepine hydrochloride.

Following the procedure of Example 4, 3-methyl-8-methoxy-7-methylsulfonyl-2,3,4,5-tetrahydro-1H-3-benzazepine hydrochloride was reacted with 48% hydrobromic acid to give 8-hydroxy-3-methyl-7-methylsulfonyl-2,3,4,5-tetrahydro-1H-3-benzazepine hydrobromide, m.p. 310° (decomp.).

EXAMPLE 7

8-Hydroxy-7-trifluoromethylsulfonyl-2,3,4,5-tetrahydro-1H-3-benzazepine and 8-hydroxy-7-trifluoromethylsulfinyl-2,3,4,5-tetrahydro-1H-3-benzazepine 3-Acetyl-8-methoxy-7-methylthio-2,3,4,5-tetrahydro-1H-3-benzazepine (12 g, 0.05 mol) prepared substantially as in Example 4, Method B, is dissolved in ethanol-free chloroform (250 ml) containing cumene (10 g) and stirred in the dark. Chlorine is passed through the solution for 48 hours and the mixture is concentrated in vacuo to give 3-acetyl-8-methoxy-7-trichloromethylthio-2,3,4,5-tetrahydro-1H-3-benzazepine.

3-Acetyl-8-methoxy-7-trichloromethylthio-2,3,4,5-tetrahydro-1H-3-benzazepine (5.5 g, 0.016 mol), antimony trifluoride (15 g, 0.09 ml) and antimony pentachloride (1.5 g, 0.005 mol) are heated and stirred at 90° for 24 hours. The resulting mixture is partitioned between chloroform and 3N hydrochloric acid. The chloroform phase is concentrated in vacuo to give 3-acetyl-8-methoxy-7-trifluoromethylthio-2,3,4,5-tetrahydro-1H-3-benzazepine.

Following the procedure of Examples 4 Method B and 5, 3-acetyl-8-methoxy-7-trifluoromethylthio-2,3,4,5-tetrahydro-1H-3-benzazepine is reacted with 3-chloroperbenzoic acid and then hydrolyzed with 3N hydrochloric acid to give:

8-methoxy-7-trifluoromethylsulfonyl-2,3,4,5-tetrahydro-1H-3-benzazepine hydrochloride and
8-methoxy-7-trifluoromethylsulfinyl-2,3,4,5-tetrahydro-1H-3-benzazepine hydrochloride.

These 8-methoxy compounds are treated with 48% hydrobromic acid to give:
8-hydroxy-7-trifluoromethylsulfonyl-2,3,4,5-tetrahydro-1H-3-benzazepine hydrobromide and
8-hydroxy-7-trifluoromethylsulfinyl-2,3,4,5-tetrahydro-1H-3-benzazepine hydrobromide.

EXAMPLE 8

7-Hydroxy-6-methylsulfonyl-2,3,4,5-tetrahydro-1H-3-benzazepine

A solution of 3-acetyl-7-methoxy-2,3,4,5-tetrahydro-1H-3-benzazepine (2.3 g, 0.01 m) in acetic acid (20 ml) was treated with a solution of bromine (1.8 g, 0.011 m) in acetic acid (10 ml). The mixture was warmed to 70° for 1.5 hours, concentrated in vacuo and partitioned between water and ethyl acetate. The ethyl acetate phase was washed, dried with sodium sulfate and concentrated in vacuo to give 3-acetyl-8-bromo-7-methoxy-2,3,4,5-tetrahydro-1H-3-benzazepine. NMR (CDCl$_3$) 6.7, 7.3; aryl protons.

Following the procedure of Example 1, 3-acetyl-8-bromo-7-methoxy-2,3,4,5-tetrahydro-1H-3-benzazepine is converted to 3-acetyl-8-bromo-6-chlorosulfonyl-7-methoxy-2,3,4,5-tetrahydro-1H-3-benzazepine and by the procedure of Example 4, this chlorosulfonyl compound is converted to 3-acetyl-8-bromo-7-methoxy-6-methylsulfonyl-2,3,4,5-tetrahydro-1H-3-benzazepine.

A mixture of 3-acetyl-8-bromo-7-methoxy-6-methylsulfonyl-2,3,4,5-tetrahydro-1H-3-benzazepine (3.7 g, 0.01 m) and 10% palladium-on-carbon (0.37 g) in methanol (50 ml) is stirred in an atmosphere of hydrogen (60 psi) until uptake is complete. The mixture is degassed, filtered and concentrated in vacuo to give 3-acetyl-7-methoxy-6-methylsulfonyl-2,3,4,5-tetrahydro-1H-3-benzazepine.

Following the procedure of Example 4, 3-acetyl-7-methoxy-6-methylsulfonyl-2,3,4,5-tetrahydro-1H-3-benzazepine is treated with hydrochloric acid to give 7-methoxy-6-methylsulfonyl-2,3,4,5-tetrahydro-1H-3-benzazepine hydrochloride which is treated with 48% hydrobromic acid to give 7-hydroxy-6-methylsulfonyl-2,3,4,5-tetrahydro-1H-3-benzazepine hydrobromide.

EXAMPLE 9

8-Hydroxy-3-methyl-6-methylsulfonyl-2,3,4,5-tetrahydro-1H-3-benzazepine and 6-hydroxy-3-methyl-8-methylsulfonyl-1H-3-benzazepine A mixture of 5-bromo-3-hydroxytoluene (93 g, 0.5 m) and sodium hydroxide (21 g, 0.5 m) in water (200 ml) is stirred at 10°, treated with dimethyl sulfate (63 g, 0.5 m) over 1 hour, refluxed for 2 hours and cooled. The mixture is diluted with water and extracted with ether. The ether extract is washed, dried with sodium sulfate and concentrated in vacuo to give 5-bromo-3-methoxytoluene.

A mixture of 5-bromo-3-methoxytoluene (20 g, 0.1 m), N-bromosuccinimide (17.8 g, 0.1 m) and dibenzoyl peroxide in carbon tetrachloride (200 ml) is heated to reflux and irradiated with a sunlamp. The mixture is cooled, filtered and concentrated in vacuo to give 5-bromo-3-methoxybenzyl bromide.

A mixture of the crude benzyl bromide and sodium cyanide (4.9 g, 0.1 m) in ethanol (500 ml) is stirred at 65° for 16 hours. The mixture is cooled, filtered and concentrated in vacuo. The residue is partitioned between water and chloroform and the chloroform phase is washed, dried with sodium sulfate and concentrated in vacuo to afford 5-bromo-3-methoxyphenylacetonitrile.

A mixture of 5-bromo-3-methoxyphenylacetonitrile (22.6 g, 0.1 m) and 10% aqueous sodium hydroxide (300 ml) in ethanol (225 ml) is heated to 95° for 18 hours. The mixture is concentrated in vacuo, acidified with 10% hydrochloric acid and extracted with ethyl acetate. The ethyl acetate extract is washed, dried with sodium sulfate and concentrated in vacuo to give 5-bromo-3-methoxyphenylacetic acid.

Following the general procedure of Example 1, 5-bromo-3-methoxyphenylacetic acid is converted to a mixture of 6-bromo-8-methoxy-2,3,4,5-tetrahydro-1H-3-benzazepine and 8-bromo-6-methoxy-2,3,4,5-tetrahydro-1H-3benzazepine. The isomers are separated by preparative HPLC.

Each isomer (2.6 g, 0.01 m) is dissolved in 98% formic acid (50 ml) and 37% aqueous formaldehyde (10 ml), then heated to 95° for 5 hours, poured into ice water, basified with 10% aqueous sodium hydroxide and extracted with ethyl acetate. The ethyl acetate extract is washed, dried with sodium sulfate and concentrated in vacuo to give, individually 6-bromo-8-methoxy-3-methyl-2,3,4,5-tetrahydro-1H-3-benzazepine and 8-bromo-6-methoxy-3-methyl-2,3,4,5-tetrahydro-1H-3-benzazepine.

A solution of 6-bromo-8-methoxy-3-methyl-2,3,4,5-tetrahydro-1H-3-benzazepine (2.7 g, 0.01 m) in toluene (30 ml) is added to a solution of n-butyl lithium (0.044 m) in toluene (15 ml) stirred at −78°. The mixture is stirred for thirty minutes, treated with a solution of methyl disulfide (8.2 g, 0.087 m) in toluene (10 ml), stirred for fifteen minutes and poured into water (125 ml). The mixture is acidified with 10% hydrochloric acid and the aqueous phase is washed with ether, made alkaline with aqueous sodium hydroxide and extracted with ethyl acetate. The ethyl acetate extract is washed, dried with sodium sulfate and concentrated in vacuo to give 8-methoxy-3-methyl-6-methylthio-2,3,4,5-tetrahydro-1H-3-benzazepine.

Following the procedure of Example 4, Method B, 8-methoxy-3-methyl-6-methylthio-2,3,4,5-tetrahydro-1H-3-benzazepine is converted to 8-methoxy-3-methyl-6-methylsulfonyl-2,3,4,5-tetrahydro-1H-3-benzazepine hydrochloride which is treated with hydrobromic acid to give 8-hydroxy-3-methyl-6-methylsulfonyl-2,3,4,5-tetrahydro-1H-3-benzazepine hydrobromide.

By the same procedure, 8-bromo-6-methoxy-3-methyl-2,3,4,5-tetrahydro-1H-3-benzazepine is converted to 6-methoxy-3-methyl-8-methylsulfonyl-1H-3-benzazepine hydrochloride which is treated with 48% hydrobromic acid to give 6-hydroxy-3-methyl-8-methylsulfonyl-1H-3-benzazepine hydrobromide.

EXAMPLE 10

6-Methoxy-9-methylsulfonyl-2,3,4,5-tetrahydro-1H-3-benzazepine and 6-hydroxy-9-methylsulfonyl-2,3,4,5-tetrahydro-1H-3-benzazepine A mixture of 2,3-dimethylanisole (2 g, 0.014 m), N-bromosuccinimide (5.3 g, 0.03 m) and dibenzoyl peroxide (8 mg) in carbon tetrachloride (50 ml) was heated to reflux and irradiated with a sunlamp for 45 minutes. The mixture was cooled, filtered and concentrated in vacuo to afford 2,3-bis(bromomethyl)anisole which was triturated with methanol (m.p. 70°).

A solution of 2,3-bis(bromomethyl)anisole (43 g, 0.146 m) in dimethylsulfoxide (150 ml) was added to a stirred mixture of sodium cyanide (28.7 g, 0.585 m) and dimethylsulfoxide (200 ml). The mixture was cooled so that the internal temperature did not exceed 60° during addition of the dibromide. The mixture was stirred for one hour at 50°, then poured into ice water and filtered to give 3-methoxy-1,2-phenylene-diacetonitrile.

A mixture of 3-methoxy-1,2-phenylenediacetonitrile (44 g, 0.236 m) and Raney nickel in ethanol saturated with ammonia was heated to 100° in a hydrogen atmosphere (75 atm) for 2 hours. The mixture was cooled, deagassed, filtered, concentrated in vacuo and partitioned between 10% aqueous hydrochloric acid and ethyl acetate-ether (1:1). The aqueous phase was basified with 40% aqueous sodium hydroxide and extracted with ethyl acetate. The ethyl acetate extract was washed with brine, dried with magnesium sulfate and concentrated in vacuo. The residue was treated with maleic acid and crystallized from acetonitrile to give 6-methoxy-2,3,4 5-tetrahydro-1H-3-benzazepine maleate, m.p. 153°–155°.

Following the procedures of Examples 1 and 4, 6-methoxy-2,3,4,5-tetrahydro-1H-3-benzazepine is converted via 3-acetyl-6-methoxy-9-methylsulfonyl-2,3,4,5-tetrahydro-1H-3-benzazepine to 6-methoxy-9-methylsulfonyl-2,3,4,5-tetrahydro-1H-3-benzazepine hydrochloride and then on treatment with hydrobromic acid to 6-hydroxy-9-methylsulfonyl-2,3,4,5-tetrahydro-1H-3-benzazepine hydrobromide.

EXAMPLE 11

6-Hydroxy-7-methylsulfonyl-2,3,4,5-tetrahydro-1H-3-benzazepine

Following the procedure of Examples 1 and 8, 6-methoxy-2,3,4,5-tetrahydro-1H-3-benzazepine is converted via 3-acetyl-6-methoxy-7-methylsulfonyl-9-bromo-2,3,4,5-tetrahydro-1H-3-benzazepine to 6-methoxy-7-methylsulfonyl-2,3,4,5-tetrahydro-1H-3-benzazepine hydrochloride which is treated with hydrobromic acid to give 6-hydroxy-7-methylsulfonyl-2,3,4,5-tetrahydro-1H-3-benzazepine hydrobromide.

EXAMPLE 12

8-Acetoxy-7-methylsulfonyl-2,3,4,5-tetrahydro-1H-3-benzazepine

A mixture of 8-hydroxy-7-methylsulfonyl-2,3,4,5-tetrahydro-1H-3-benzazepine hydrobromide (3.2 g, 0.01 m) in trifluoroacetic acid (25 ml) is stirred at 25° and treated with acetyl bromide (1.4 g, 0.011 m). The mixture is stirred at 25° and concentrated in vacuo to give 8-acetoxy-7-methylsulfonyl-2,3,4,5-tetrahydro-1H-3-benzazepine hydrobromide.

EXAMPLE 13

8-Hydroxy-7-methylsulfonyl-2,3,4,5-tetrahydro-1H-3-benzazepine

8-Hydroxy-7-methylsulfonyl-2,3,4,5-tetrahydro-1H-3-benzazepine hydrobromide was treated with ammonium hydroxide. The resulting mixture was filtered to give 8-hydroxy-7-methylsulfonyl-2,3,4,5-tetrahydro-1H-3-benzazepine, m.p. 241°-242°. This was treated with methanesulfonic acid to give the methanesulfonate, m.p. 267°-269°.

EXAMPLE 14

3-Allyl-8-hydroxy-7-methylsulfonyl-2,3,4,5-tetrahydro-1H-3-benzazepine

Allyl bromide is added to a mixture of 8-hydroxy-7-methylsulfonyl-2,3,4,5-tetrahydro-1H-3-benzazepine (one equivalent) in acetone containing potassium carbonate and the mixture is stirred at 5°, then at 25° and finally at reflux. The mixture is then poured into water, extracted with ethyl acetate and treated with ethereal hydrogen chloride to give 3-allyl-8-hydroxy-7-methylsulfonyl-2,3,4,5-tetrahydro-1H-3-benzazepine hydrochloride.

EXAMPLE 15

7-Methylsulfonyl-2,3,4,5-tetrahydro-1H-3-benzazepine

Following the procedure of Examples 1 and 4, 2,3,4,5-tetrahydro-1H-3-benzazepine was converted to 3-acetyl-7-chlorosulfonyl-2,3,4,5-tetrahydro-1H-3-benzazepine and then to 3-acetyl-7-methylsulfonyl-2,3,4,5-tetrahydro-1H-3-benzazepine which was hydrolyzed with hydrochloric acid to give 7-methylsulfonyl-2,3,4,5-tetrahydro-1H-3-benzazepine hydrochloride, m.p. 275°-277° C.

EXAMPLE 16

7-Methylsulfinyl-2,3,4,5-tetrahydro-1H-3-benzazepine

Following the procedure of Examples 4 and 5, 3-acetyl-7-chlorosulfonyl-2,3,4,5-tetrahydro-1H-3-benzazepine is converted to 3-acetyl-7-methylthio-2,3,4,5-tetrahydro-1H-3-benzazepine and then to 3-acetyl-7-methylsulfinyl-2,3,4,5-tetrahydro-1H-3-benzazepine which is hydrolyzed with dilute hydrochloric acid to give 7-methylsulfinyl-2,3,4,5-tetrahydro-1H-3-benzazepine hydrochloride.

EXAMPLE 17

8-Methyl-7-methylsulfonyl-2,3,4,5-tetrahydro-1H-3benzazepine and
8-methyl-7-methylsulfinyl-2,3,4,5-tetrahydro-1H-3-benzazepine Following the procedure of Examples 1, 15 and 16, 3-methylphenylacetic acid is converted to 3-acetyl-7-methyl-2,3,4,5-tetrahydro-1H-3-benzazepine and then to 3-acetyl-8-methyl-7-chlorosulfonyl-2,3,4,5-tetrahydro-1H-3-benzazepine which is converted to 8-methyl-7-methylsulfonyl-2,3,4,5-tetrahydro-1H-3-benzazepine hydrochloride or 8-methyl-7-methylsulfinyl-2,3,4,5-tetrahydro-1H-3-benzazepine hydrochloride.

EXAMPLE 18

8-Hydroxy-7-propylsulfonyl-2,3,4,5-tetrahydro-1H-3-benzazepine

By the procedure of Example 4, Method B using propyl iodide in place of methyl iodide, 3-acetyl-8-methoxy-7-propylsulfonyl-2,3,4,5-tetrahydro-1H-3-benzazepine was obtained which on treatment with hydrobromic acid gave 8-hydroxy-7-propylsulfonyl-2,3,4,5-tetrahydro-1H-3-benzazepine hydrobromide, m.p. 177°-180° C.

EXAMPLE 19

8-Chloro-7-methylsulfonyl-2,3,4,5-tetrahydro-1H-3-benzazepine and
8-chloro-7-methylsulfinyl-2,3,4,5-tetrahydro-1H-3-benzazepine Following the procedure of Examples 15 and 16, 7-chloro-2,3,4,5-tetrahydro-1H-3-benzazepine is converted to 3-acetyl-8-chloro-7-chlorosulfonyl-2,3,4,5-tetrahydro-1H-3-benzazepine and then to 8-chloro-7-methylsulfonyl-2,3,4,5-tetrahydro-1H-3-benzazepine hydrochloride or 8-chloro-7-methylsulfinyl-2,3,4,5-tetrahydro-1H-3-benzazepine hydrochloride.

EXAMPLE 20

8-Hydroxy-7-methylsulfonyl-2,3,4,5-tetrahydro-1H-3-benzazepine methanesulfonate (10 mg) is mixed with 75 mg of lactose and 2 mg of magnesium stearate. The resulting mixture is filled into a hard gelatin capsule.

We claim:
1. A compound of the formula:

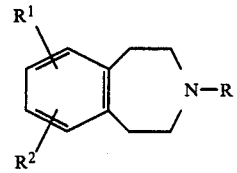

in which:
R is hydrogen, or $C_1$–$C_6$alkyl or $C_3$–$C_5$alkenyl;
$R^1$ is $SOR^3$, $SO_2R^3$ or $SO_2NR^4R^5$;
$R^2$ is hydrogen, halogen, $CF_3$, $C_1$–$C_6$alkyl or $R^6O$—;
$R^3$ is $C_1$–$C_6$alkyl or $CF_3$;
$R^4$ and $R^5$ are hydrogen or $C_1$–$C_6$alkyl; and
$R_6$ is $C_2$–$C_6$alkyl, provided that when $R^1$ is $SO_2R^2$ is $R^6O$—, halogen, $CF_3$, or $C_1$–$C_6$alkyl, or a pharmaceutically acceptable acid addition salt thereof.

2. A compound of claim 1 in which $R^1$ is in the 7-position.

3. A compound of claim 1 in which $R^2$ is in the 8-position and $R^1$ is in the 7-position.

4. A compound of claim 1 in which $R^1$ is $SO_2R^3$ or $SO_2NR^4R^5$, $R^2$ is hydrogen or $C_2-C_6$alkoxy, $R^3$ is methyl, R is hydrogen, $R^2$ is in the 8-position and $R^1$ is in the 7-position.

5. A compound of claim 1 said compound being 7-methylsulfonyl-2,3,4,5-tetrahydro-1H-3-benzazepine.

6. A compound of claim 1 said compound being 6-sulfamoyl-2,3,4,5-tetrahydro-1H-3-benzazepine.

7. A compound of claim 1 said compound being 7-sulfamoyl-2,3,4,5-tetrahydro-1H-3-benzazepine.

8. A pharmaceutical composition for treatment of gastrointestinal motility disorders comprising a pharmaceutical carrier and, in an amount sufficient to produce said activity, a compound of claim 1.

9. A pharmaceutical composition for treatment of gastrointestinal motility disorders comprising a pharmaceutical carrier and, in an amount sufficient to produce said activity, the compound of claim 5.

10. A pharmaceutical composition for treatment of gastrointestinal motility disorders comprising a pharmaceutical carrier and, in an amount sufficient to produce said activity, a compound of claim 6.

11. A pharmaceutical composition for treatment of gastrointestinal motility disorders comprising a pharmaceutical carrier and, in an amount sufficient to produce said activity, a compound of claim 7.

12. A method of treating gastrointestinal motility disorders which comprises administering internally to a subject in need of said treatment an effective but nontoxic amount of a compound of claim 1.

13. A method of treating gastrointestinal motility disorders which comprises administering internally to a subject in need of said treatment an effective but nontoxic amount of the compound of claim 5.

14. A method of treating gastrointestinal motility disorders which comprises administering internally to a subject in need of said treatment an effective amount of a composition of claim 10.

15. A method of treating gastrointestinal motility disorders which comprises administering internally to a subject in need of said treatment an effective amount of a composition of claim 11.

16. A method of claim 12 in which gastroesophageal reflux disease of delayed gastric emptying is treated.

17. A method of claim 13 in which gastroesophageal reflux disease of delayed gastric emptying is treated.

18. A method of treating or preventing emesis which comprises administering internally to a subject in need of said treatment an effective but nontoxic amount of a compound of the formula:

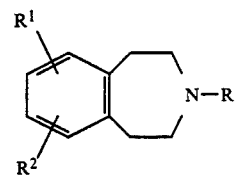

in which:

R is hydrogen, $C_1-C_6$alkyl or $C_3-C_5$alkenyl;

$R^1$ is $SOR^3$, $SO_2R^3$ or $SO_2NR^4R^5$;

$R^2$ is hydrogen, halogen, $CF_3$, $C_1-C_6$alkyl or $R^6O-$;

$R^3$ is $C_1-C_6$alkyl or trifluoromethyl;

$R^4$ and $R_5$ are hydrogen or $C_1-C_6$alkyl; and $R^6$ is hydrogen, $C_1-C_6$alkyl or $C_1-C_6$alkanoyl, provided that when $R^1$ is $SO_2NH_2$, $R^2$ is $R^6O-$, halogen, $CF_3$ or $C_1-C_6$alkyl, or a pharmaceutically acceptable acid addition salt thereof.

19. A method of treating or preventing emesis which comprises administering internally to a subject in need of said treatment an effective but non-toxic amount of a compound of claim 18 in which said compound is 8-hydroxy-7-methylsulfonyl-2,3,4,5-tetrahydro-1H-3-benzazepine.

* * * * *

UNITED STATES PATENT AND TRADEMARK OFFICE
CERTIFICATE OF CORRECTION

PATENT NO. : 4,824,839
DATED : April 25, 1989
INVENTOR(S) : William E. Bondinell; Herbert S. Ormsbee, III It is certified that error appears in the above-identified patent and that said Letters Patent is hereby corrected as shown below:

Column 1, line 44 : delete "$SO_1NB_4R^5$" and replace with -- $SO_2NR^4R^5$ -- .

Column 1, line 49 : delete "$SO_2NH_2^5$" and replace with -- $SO_2NH_2$, -- .

Column 2, line 35 : "$B^{10}$" should be -- $R^{10}$ -- .

Column 14, line 64: delete "$SO_2$" and replace with -- $SO_2NH_2$, -- .

Column 16,
Claim 17, line 10 : delete "of" and replace with -- or -- .
Column 16,
Claim 18, line 29 : "$R_5$" should be -- $R^5$ -- .

Signed and Sealed this

Ninth Day of January, 1990

*Attest:*

JEFFREY M. SAMUELS

*Attesting Officer*   *Acting Commissioner of Patents and Trademarks*